United States Patent
O'Carroll et al.

(10) Patent No.: US 10,842,625 B2
(45) Date of Patent: Nov. 24, 2020

(54) ANNULOPLASTY IMPLANT

(71) Applicant: Medtentia International Ltd Oy, Espoo (FI)

(72) Inventors: Ger O'Carroll, Castlebaldwin (IE); Mark Pugh, Coolaney (IE); Adrian Moran, Ballinfull (IE); Chen Xie, Newbridge (IE)

(73) Assignee: Medtentia International Ltd Oy, Espoo (FI)

( * ) Notice: Subject to any disclaimer, the term of this patent is extended or adjusted under 35 U.S.C. 154(b) by 76 days.

(21) Appl. No.: 16/071,901

(22) PCT Filed: Oct. 13, 2016

(86) PCT No.: PCT/EP2016/074613
§ 371 (c)(1),
(2) Date: Jul. 20, 2018

(87) PCT Pub. No.: WO2017/125170
PCT Pub. Date: Jul. 27, 2017

(65) Prior Publication Data
US 2019/0021859 A1   Jan. 24, 2019

Related U.S. Application Data

(60) Provisional application No. 62/281,751, filed on Jan. 22, 2016.

(51) Int. Cl.
*A61F 2/24* (2006.01)
*A61F 2/30* (2006.01)

(52) U.S. Cl.
CPC .. *A61F 2/2445* (2013.01); *A61F 2002/30004* (2013.01); *A61F 2230/0091* (2013.01)

(58) Field of Classification Search
CPC ........ A61F 2/24; A61F 2/2418; A61F 2/2442; A61F 2/2445; A61F 2/2448; A61F 2230/0091
See application file for complete search history.

(56) References Cited

U.S. PATENT DOCUMENTS

| | | | | |
|---|---|---|---|---|
| 5,104,407 A | * | 4/1992 | Lam | A61F 2/2448 623/2.36 |
| 5,201,880 A | * | 4/1993 | Wright | A61F 2/2448 623/2.37 |
| 5,306,296 A | * | 4/1994 | Wright | A61F 2/2409 623/2.37 |
| 5,662,704 A | * | 9/1997 | Gross | A61F 2/2412 623/2.1 |
| 5,674,279 A | * | 10/1997 | Wright | A61F 2/2409 623/2.37 |

(Continued)

*Primary Examiner* — Alvin J Stewart
(74) *Attorney, Agent, or Firm* — Patent Grove, LLC; Tomas Friend

(57) ABSTRACT

An annuloplasty implant comprises a plurality of individual wires, each extending in a longitudinal direction of the implant between first and second opposite ends of the implant. A locking unit arranged at at least one of the ends comprises a locking structure connected to the plurality of individual wires, thereby collecting said plurality of individual wires together at at least one of the ends. The locking structure is configured to allow a relative movement between at least two of the plurality of individual wires inside the locking structure.

15 Claims, 6 Drawing Sheets

(56) References Cited

U.S. PATENT DOCUMENTS

| | | | | |
|---|---|---|---|---|
| 5,716,397 A * | 2/1998 | Myers | | A61F 2/2445 623/2.36 |
| 6,066,160 A * | 5/2000 | Colvin | | A61B 17/0487 606/151 |
| 6,348,068 B1 * | 2/2002 | Campbell | | A61F 2/2418 623/1.15 |
| 7,635,387 B2 * | 12/2009 | Reuter | | A61F 2/2451 623/2.11 |
| 8,287,591 B2 * | 10/2012 | Keidar | | A61F 2/2445 623/2.36 |
| 9,089,424 B2 * | 7/2015 | Paolitto | | A61F 2/2442 |
| 9,180,006 B2 * | 11/2015 | Keranen | | A61F 2/2448 |
| 9,326,858 B2 * | 5/2016 | Migliazza | | A61F 2/2448 |
| 9,474,599 B2 * | 10/2016 | Keranen | | A61F 2/2442 |
| 9,636,219 B2 * | 5/2017 | Keidar | | A61F 2/2445 |
| 9,668,859 B2 * | 6/2017 | Kheradvar | | A61F 2/2439 |
| 10,034,749 B2 * | 7/2018 | Spence | | A61F 2/2418 |
| 10,039,637 B2 * | 8/2018 | Maimon | | A61F 2/2433 |
| 10,052,198 B2 * | 8/2018 | Chau | | A61F 2/243 |
| 10,195,028 B2 * | 2/2019 | Hosmer | | A61F 2/2418 |
| 10,226,339 B2 * | 3/2019 | Spence | | A61F 2/2418 |
| 10,463,479 B2 * | 11/2019 | Manash | | A61F 2/2436 |
| 2003/0083742 A1 * | 5/2003 | Spence | | A61F 2/2418 623/2.16 |
| 2005/0070999 A1 * | 3/2005 | Spence | | A61F 2/2418 623/2.37 |
| 2005/0075727 A1 * | 4/2005 | Wheatley | | A61F 2/2412 623/2.17 |
| 2006/0015179 A1 * | 1/2006 | Bulman-Fleming | | A61F 2/2445 623/2.36 |
| 2007/0179603 A1 * | 8/2007 | Wright | | A61F 2/2445 623/2.36 |
| 2009/0054982 A1 * | 2/2009 | Cimino | | A61F 2/08 623/13.19 |
| 2015/0039082 A1 * | 2/2015 | Keranen | | A61F 2/2442 623/2.11 |
| 2016/0262741 A1 * | 9/2016 | Gilmore | | A61F 2/2442 |

* cited by examiner

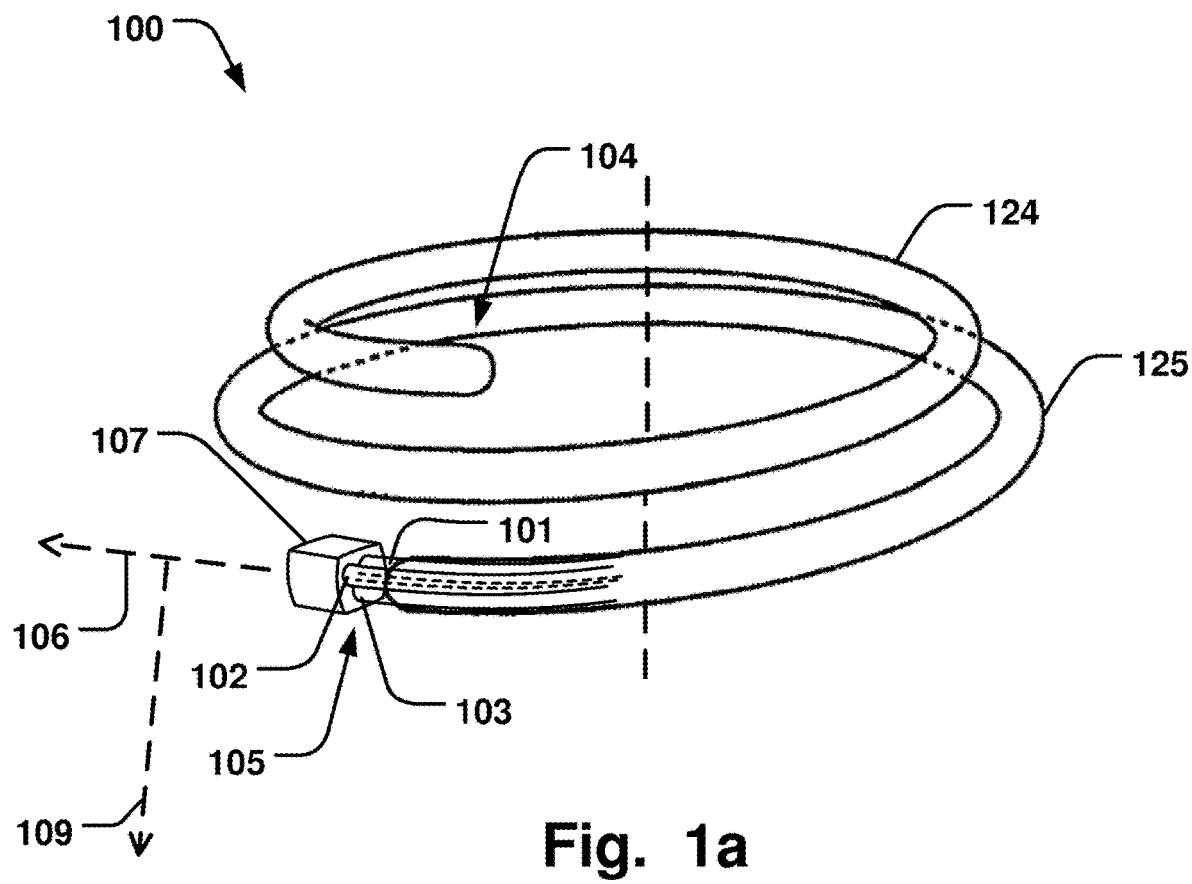
Fig. 1a
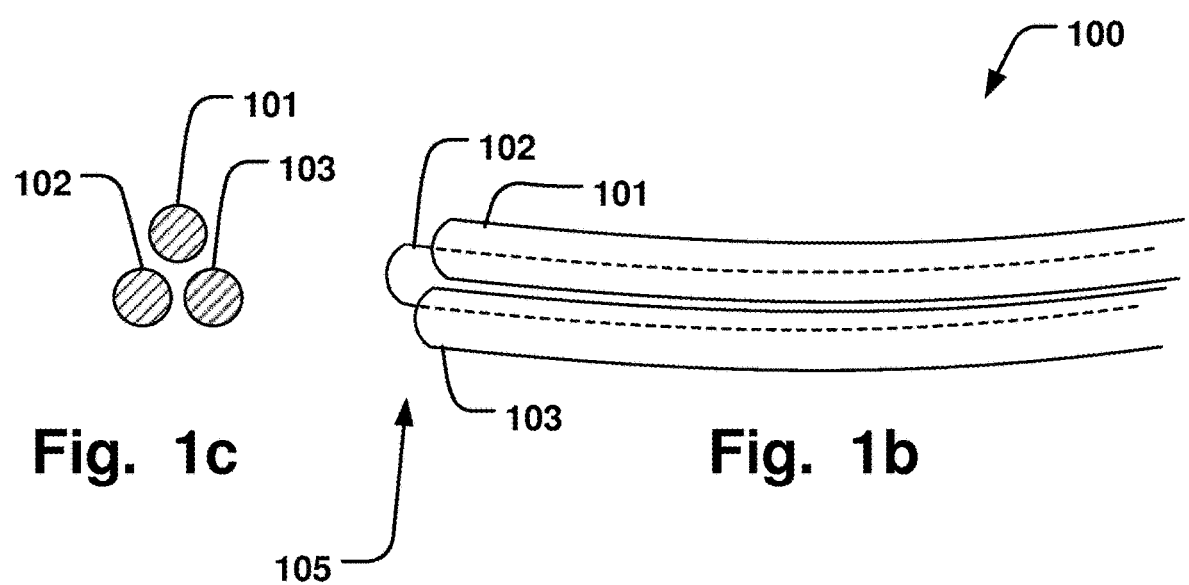
Fig. 1c
Fig. 1b

ANNULOPLASTY IMPLANT

FIELD OF THE INVENTION

This invention pertains in general to the field of cardiac valve replacement and repair. More particularly the invention relates to an annuloplasty implant, such as an annuloplasty ring or helix, for positioning at the heart valve annulus.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure.

Annuloplasty rings delivered via a catheter needs to be able to assume a stretched or elongated form when constrained by the catheter during guiding to the target site, as well as the desired shape along the annulus once pushed out of the catheter. At the same time, the annuloplasty ring needs to be strong and durable over long-term implantation, as well as having a certain flexibility.

A problem with prior art annuloplasty implants is the compromise between strength of the ring and the ability to conform to the catheter during delivery as well as the desired shape once implanted. This may lead to difficulties in navigating and delivering the ring to the target site, due to the less-than-optimal characteristics of the ring, which in turn entails a higher risk to the patient. A further problem of prior art devices is the lack of flexibility of the implant in certain situations, which impedes optimal functioning when implanted in the moving heart, or adaptability to varying anatomies.

The above problems may have dire consequences for the patient and the health care system. Patient risk is increased.

Hence, an improved annuloplasty implant would be advantageous and in particular allowing for improved properties during the initial implantation phase, and long term functioning.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention an annuloplasty implant is provided comprising a plurality of individual wires each extending in a longitudinal direction of said implant between first and second opposite ends of said implant, a locking unit arranged at at least one of said first and second ends, said locking unit comprises a locking structure being connected to said plurality of individual wires, thereby collecting said plurality of individual wires together at at least one of said first and second ends, said locking structure being configured to allow a relative movement between at least two of said plurality of individual wires inside said locking structure.

Further embodiments of the invention are defined in the dependent claims, wherein features for the second and subsequent aspects of the invention are as for the first aspect mutatis mutandis.

Some embodiments of the invention provide for a more flexible implant.

Some embodiments of the invention provide for a low-profile implant.

Some embodiments of the invention provide for facilitated delivery of the implant to the target site.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1a is an illustration of an annuloplasty implant according to an embodiment of the invention;

FIG. 1b is an illustration of an annuloplasty implant according to an embodiment of the invention in a detail view from FIG. 1a;

FIG. 1c is an illustration of a detail of the annuloplasty implant in FIG. 1b in a cross-sectional view, according to an embodiment of the invention;

FIG. 2a is an illustration of an annuloplasty implant according to an embodiment of the invention in a detail view from FIG. 1a;

DESCRIPTION OF EMBODIMENTS

Figure 2A:
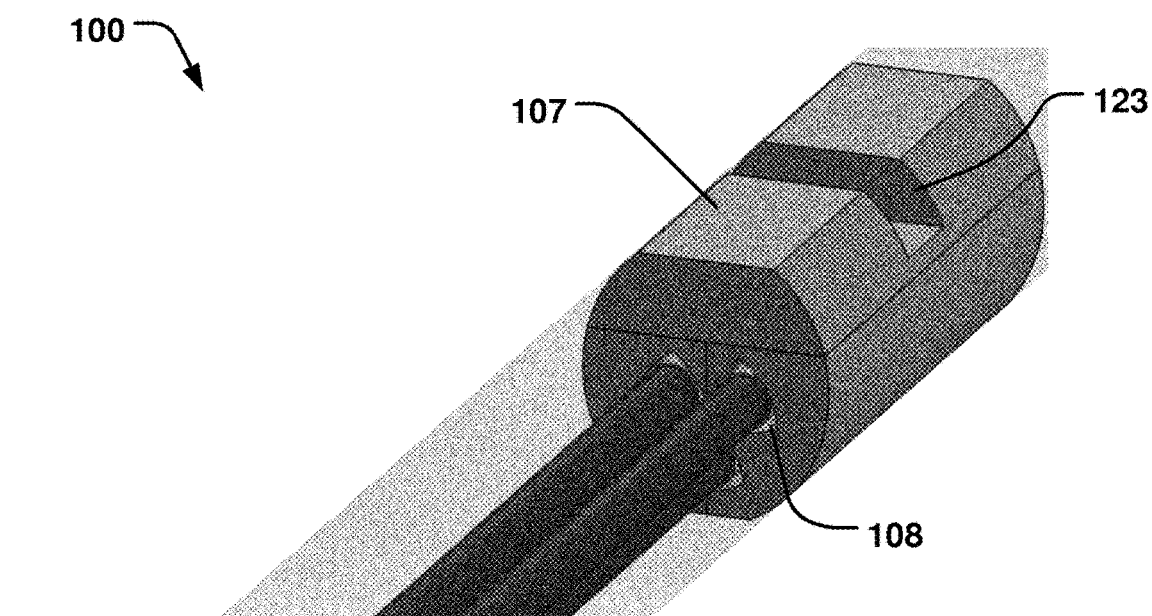

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

FIG. 1a shows an annuloplasty implant 100 comprising a plurality of individual wires 101, 102, 103, each extending in a longitudinal direction 106 of the implant between first and second opposite ends 104, 105, of the implant. A locking unit 107, 107', is arranged at at least one of the first and second ends. The locking unit comprises a locking structure 108, seen in more detail in FIG. 2a, being connected to the plurality of individual wires, thereby collecting the plurality of individual wires together at at least one of the first and second ends. The locking structure is configured to allow a relative movement between at least two of the plurality of individual wires inside the locking structure. By allowing a relative movement between the wires, the force exerted by the wires on each other is reduced when moving the implant between a stretched and collapsed (circular) shape, thereby reducing the resistance, i.e. the amount of force required, for stretching the implant to the stretched state for positioning inside a delivery catheter. The implant can also be more easily positioned at different annulus with different geometries, since it can be more easily manipulated to the desired shape. Also, one the implant has been positioned at the specific annulus, the implant can be more flexible, and thereby adapt to movement of the beating heart, since less force is required to change the shape of the implant. Thus manipulating the implant between various shapes is facilitated due to the reduced force required, while avoiding to reduce the cross-sectional profile of the implant (trying to reduce the force required to manipulate the shape of the material) that can cause less structural stability and/or reduced ability to be fixated at the anatomy. Thus structural stability can be maintained, while having a freely movable and conformable implant.

The relative movement may be a rotating movement. I.e. the individual wires may rotate relative to each other. The ends 115, 116, 117, of the wires are e.g. seen in FIG. 3, and the ends may thus rotate relative to each other inside the locking structure.

The relative movement may alternatively, or in addition, be a sliding movement in the longitudinal direction 106. This may further facilitate individual movement of the wires, and reduce the force required to manipulate the implant between various shapes.

The locking structure may comprise a sliding surface 110 that is able to lie in contact with at least one of the plurality of individual wires, such as a first wire 101, whereby the first wire is movable relative any other 102, 103, of the plurality of individual wires. This thus allows sliding of any of the wires against the locking structure.

Figure 4:
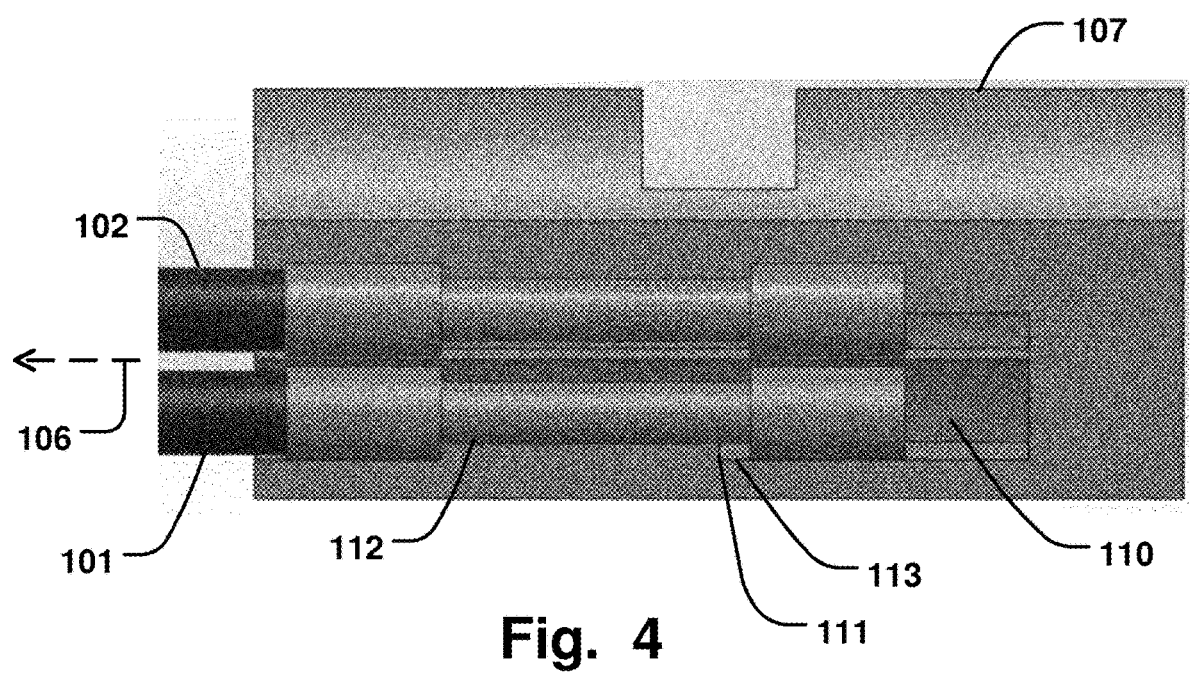
FIG. 4 is an illustration of a detail of the annuloplasty implant in FIG. 2a in a cross-sectional side view, according to an embodiment of the invention.

The sliding surface may comprise a recess or protrusion 111 that engages with a corresponding mating surface 112 of the first wire for an interlocking connection, whereby the interlocking connection allows a predefined and restricted distance of movement 113 of the first wire in the longitudinal direction 106, as illustrated in FIG. 4. This provides a secure fixation of the wires as well as the possibility of having a sliding movement of the wires relative to each other.

The protrusion 111 of the sliding surface may thus have a shorter longitudinal dimension than the mating surface, as further seen in FIG. 4. The differing lengths provides for the free distance 113 by which the respective wire can move in the locking structure. The distance 113 can be varied depending on the amount of relative movement that is desired, depending on the application, which can require more or less flexibility in the movement of the implant. As mentioned, it is also conceivable that the locking structure has a recess (not shown) in the sliding surface, instead of a protrusion. The recess may thus have a longer longitudinal dimension than the mating surface of the wire in order to allow a relative movement between the two.

Figure 2B:
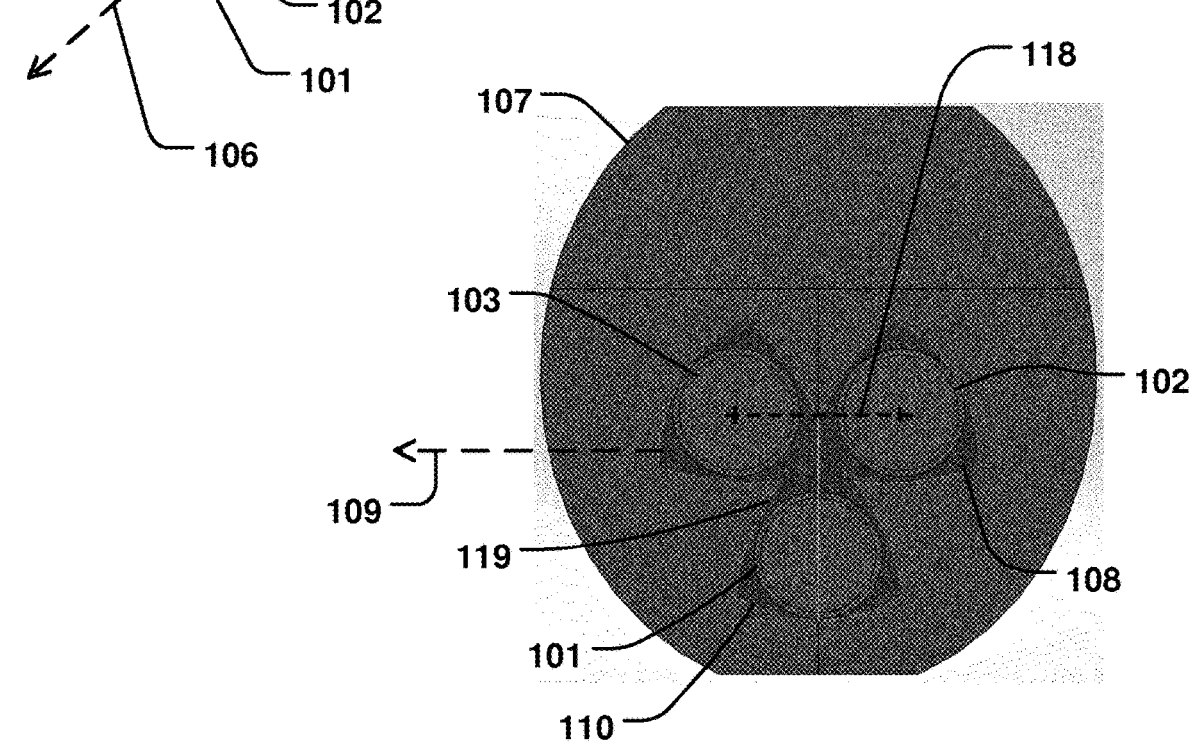
FIG. 2b is an illustration of a detail of the annuloplasty implant in FIG. 2a in a cross-sectional view, according to an embodiment of the invention.
Figure 3:
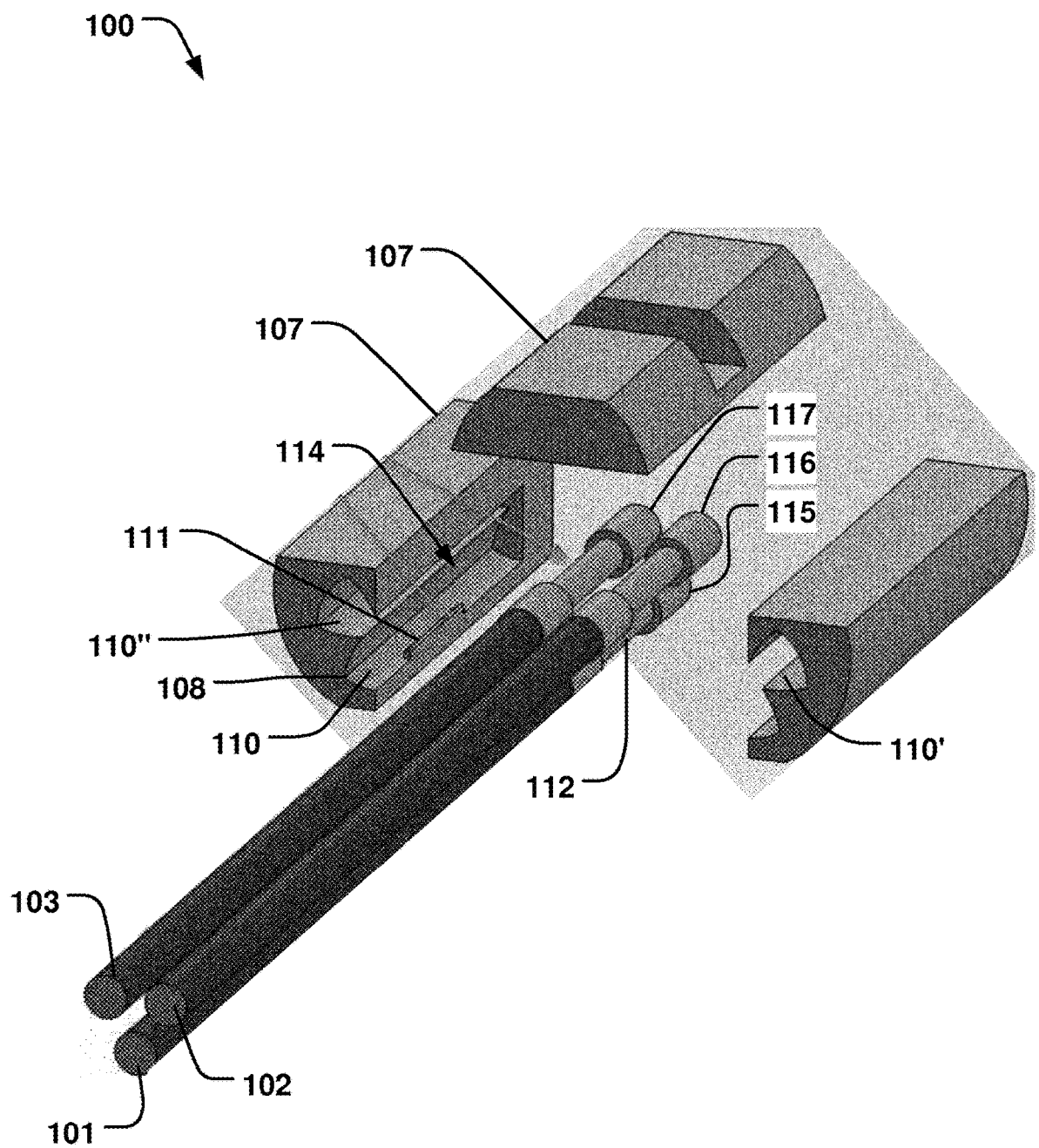
FIG. 3 is an illustration of a detail of the annuloplasty implant in FIG. 2a in an exploded perspective view, according to an embodiment of the invention.

Each of said plurality of individual wires may engage with a corresponding sliding surface 110, 110', 110", that each allows a relative movement between the plurality of individual wires, being illustrated in FIG. 3, which is an exploded view of a locking structure illustrated in FIGS. 2a-b. This provides for efficient movement of each of the wires relative to each other.

FIG. 3 also illustrates that the locking structure may comprise a hollow 114 that encloses the wire end 115, 116, 117, of each of the plurality of individual wires. This provides for a secure fixation of the wires at the end(s) of the implant, as well as sufficient freedom to arrange the sliding surfaces 110, 110', 110", inside the hollow as required to provide for the desired relative movement between the wires.

The hollow may be shaped to keep each of the plurality of individual wires spaced apart at a defined distance 118 in a radial direction 109, perpendicular to the longitudinal direction. FIG. 2b illustrates that the wires are arranged at distances 118 from eachother. Having such defined distance avoids interference between the individual wires, and ensures that the relative movement is not hindered.

The hollow may comprise a tapered void 119 that encloses at least one of the wire ends, and being tapered to narrow in a direction radially inwards from the periphery of the locking unit. The tapered shape is illustrated in FIG. 2b, and effectively keeps the end of the wire spaced apart from any of the remaining wire ends.

Figure 5:
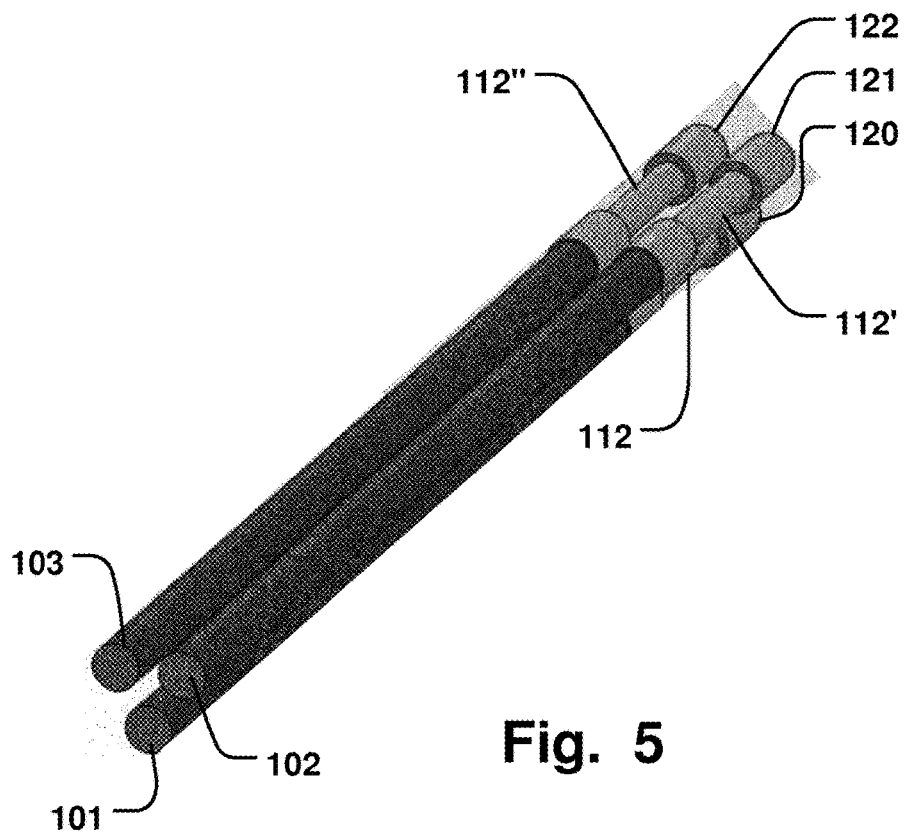
FIG. 5 is an illustration of a detail of the annuloplasty implant in FIG. 3, according to an embodiment of the invention.
Figure 6A:
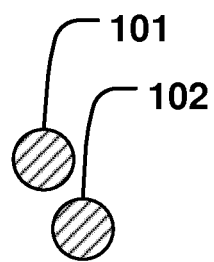
FIGS. 6a-e are illustrations of the annuloplasty implant in FIG. 1b in cross-sectional views, according to embodiments of the invention.
Figure 6B:
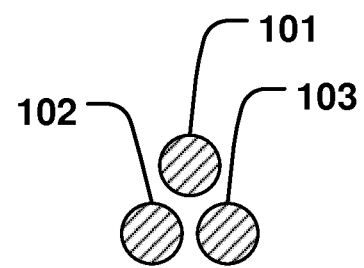
Figure 6C:
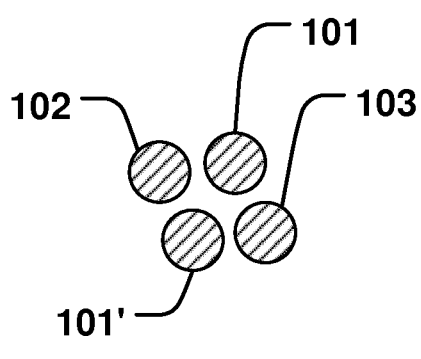
Figure 6D:
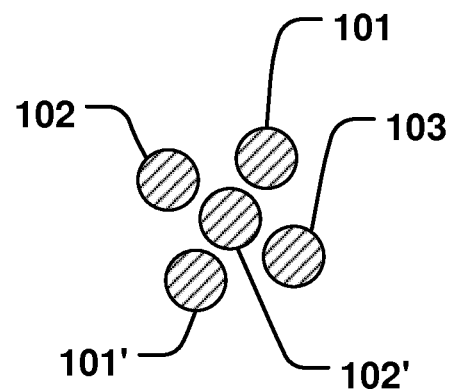
Figure 6E:
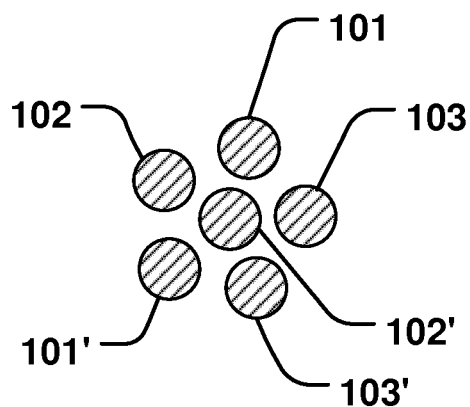

Each of the plurality of individual wires may comprise a mating surface 112, 112', 112", formed at a connecting element 120, 121, 122, attached to the ends of the plurality of individual wires, as illustrated in FIG. 5. The connecting elements provides for a well-defined surface that optimize ability for the wires to slide against corresponding sliding surfaces in the locking unit, and providing the desired relative movement.

As elucidated above, the hollow may comprise the sliding surface(s).

The annuloplasty implant may comprise at least three wires 101, 102, 103, each being individually rotatable around a rotation axis extending in the longitudinal direction. FIGS. 6a-e illustrates that the implant may comprise different numbers of individual wires, such as 2, 3, 4, 5, 6. The number of wires can be varied as desired to provide for the desired flexibility and structural stability depending on the application.

The locking unit may comprise a recess or protrusion 123 that is configured to interlock with a delivery tool, as illustrated in FIG. 2a. The locking structure may thus simultaneously function as a connecting interface to a delivery device, which provides for an overall compact implant.

Figure 7:
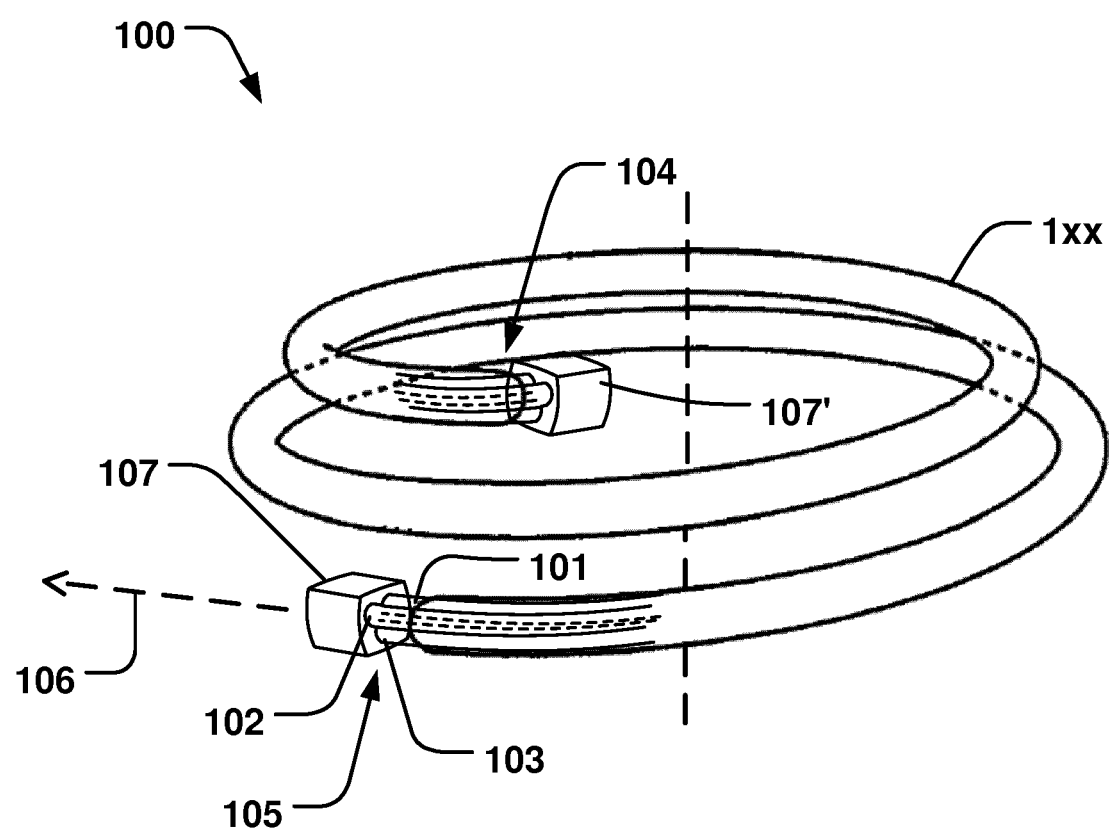
FIG. 7 is an illustration of an annuloplasty implant in a perspective view according to an embodiment of the invention.

The annuloplasty implant may comprise a catheter deliverable ring 100, wherein the ring has an elongated delivery configuration for advancement in a catheter and an implanted shape assuming a predefined configuration of the shape memory material for positioning at a heart valve annulus, as seen in FIGS. 1a and 7. At least one of the plurality of individual wires will then rotate in the locking unit when the ring moves from the elongated delivery configuration to the predefined configuration, with the advantages as described above.

The ring in the implanted shape may comprise a first 124 and second 125 support member arranged in a coiled configuration, and being adapted to be arranged on opposite sides of native heart valve leaflets to pinch the leaflets, as illustrated FIGS. 1a and 7. The implant in FIG. 7 has a locking unit that allows relative movement of the individual wires at both ends 104, 105, while the implant in FIG. 1 illustrates an example of having only one locking unit. The number of locking units may thus be varied depending on the application. Having a locking unit at both ends 104, 105, may further increase the flexibility of the implant.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty implant comprising:
   a plurality of individual wires each extending in a longitudinal direction of said implant between first and second opposite ends of said implant;
   a locking unit arranged at one or both of said first and second ends, said locking unit comprising:
   a locking structure being connected to said plurality of individual wires, thereby collecting said plurality of individual wires together at at least one of said first and second ends, said locking structure being configured to allow a relative movement between at least two of said plurality of individual wires inside said locking structure
   wherein said implant comprises a catheter deliverable ring, said ring having an elongated delivery configuration for advancement in a catheter and an implanted shape assuming a predefined configuration of a shape memory material for positioning at a heart valve annulus, and
   wherein at least one of said plurality of individual wires rotates in said locking unit when said ring moves from said elongated delivery configuration to said predefined configuration.

2. The annuloplasty implant of claim 1, wherein said relative movement is a rotating movement.

3. The annuloplasty implant of claim 2, wherein the implant comprises at least three wires, each wire being individually rotatable around a rotation axis extending in said longitudinal direction.

4. The annuloplasty implant of claim 1, wherein said relative movement is a sliding movement in said longitudinal direction.

5. The annuloplasty implant of claim 1, wherein said locking structure comprises a sliding surface in contact with at least a first wire, whereby said first wire is movable relative any other of said plurality of individual wires.

6. The annuloplasty implant of claim 5, wherein said sliding surface comprises a recess or protrusion that engages with a corresponding mating surface of said first wire for an interlocking connection, whereby said interlocking connection allows a predefined and restricted distance of movement of said first wire in said longitudinal direction.

7. The annuloplasty implant of claim 6, wherein the protrusion of said sliding surface has a shorter longitudinal dimension than said mating surface, or
   wherein the recess of said sliding surface has a longer longitudinal dimension than said mating surface.

8. The annuloplasty implant of claim 6, wherein each of said plurality of individual wires comprises a mating surface formed at a connecting element attached to the ends of said plurality of individual wires.

9. The annuloplasty implant of claim 5, wherein each of said plurality of individual wires engages with a corresponding sliding surface that each allows a relative movement between said plurality of individual wires.

10. The annuloplasty implant of claim 1, wherein said locking structure comprises a hollow that encloses the wire end of each of said plurality of individual wires.

11. The annuloplasty implant of claim 10, wherein said hollow is shaped to keep each of said plurality of individual wires spaced apart at a defined distance in a radial direction, perpendicular to said longitudinal direction.

12. The annuloplasty implant of claim 11, wherein said hollow comprises a tapered void that encloses at least one of said wire ends, and being tapered to narrow in a direction radially inwards from the periphery of said locking unit.

13. The annuloplasty implant of claim 10, wherein said hollow comprises said sliding surface.

14. The annuloplasty implant of claim 1, wherein said locking unit comprises a recess or protrusion that is configured to interlock with a delivery tool.

15. The annuloplasty implant of claim 1, wherein said ring in the implanted shape comprises a first and second support member arranged in a coiled configuration, and being adapted to be arranged on opposite sides of native heart valve leaflets to pinch said leaflets.

* * * * *